United States Patent [19]
Dec

[11] Patent Number: 6,025,920
[45] Date of Patent: Feb. 15, 2000

[54] OPACITY METER FOR MONITORING EXHAUST EMISSIONS FROM NON-STATIONARY SOURCES

[75] Inventor: John Edward Dec, Livermore, Calif.

[73] Assignee: Sandia Corporation, Livermore, Calif.

[21] Appl. No.: 08/642,974

[22] Filed: May 6, 1996

[51] Int. Cl.[7] .................................................. G01N 21/59
[52] U.S. Cl. ......................................... 356/438; 250/573
[58] Field of Search .................................. 356/436–439; 250/573, 574, 338.5

[56] References Cited

U.S. PATENT DOCUMENTS

| | | | |
|---|---|---|---|
| 4,381,153 | 4/1983 | Bohl et al. | 356/437 |
| 4,432,649 | 2/1984 | Krause | 356/438 |
| 4,647,780 | 3/1987 | Dunkel . | |
| 5,363,198 | 11/1994 | Fournier | 356/438 |
| 5,418,366 | 5/1995 | Rubin et al. | 356/438 |
| 5,583,765 | 12/1996 | Kleehammer | 250/338.5 |
| 5,604,595 | 2/1997 | Schoen | 356/438 |

FOREIGN PATENT DOCUMENTS 59-044642  3/1984  Japan .

Primary Examiner—K Hantis
Attorney, Agent, or Firm—Timothy Evans

[57] ABSTRACT

Method and apparatus for determining the opacity of exhaust plumes from moving emissions sources. In operation, a light source is activated at a time prior to the arrival of a diesel locomotive at a measurement point, by means of a track trigger switch or the Automatic Equipment Identification system, such that the opacity measurement is synchronized with the passage of an exhaust plume past the measurement point. A beam of light from the light source passes through the exhaust plume of the locomotive and is detected by a suitable detector, preferably a high-rate photodiode. The light beam is well-collimated and is preferably monochromatic, permitting the use of a narrowband pass filter to discriminate against background light. In order to span a double railroad track and provide a beam which is substantially stronger than background, the light source, preferably a diode laser, must provide a locally intense beam. A high intensity light source is also desirable in order to increase accuracy at the high sampling rates required. Also included is a computer control system useful for data acquisition, manipulation, storage and transmission of opacity data and the identification of the associated diesel engine to a central data collection center.

19 Claims, 2 Drawing Sheets

OPACITY METER FOR MONITORING EXHAUST EMISSIONS FROM NON-STATIONARY SOURCES

STATEMENT OF GOVERNMENT INTEREST

This invention was made with Government support under contract no. DE-AC04-94AL85000 awarded by the U.S. Department of Energy to Sandia Corporation. The Government has certain rights in the invention.

BACKGROUND OF THE INVENTION

This invention pertains generally to monitoring exhaust emissions from non-stationary sources and particularly to monitoring exhaust emissions from non-stationary diesel engines.

Diesel engines emit exhaust plumes that can contain particulate matter which is visually evident as opacity (i.e., smoke) and measurement of exhaust plume opacity, i.e., the particle density (number of particle/unit volume), is of importance in many areas. Regulatory agencies, both state and Federal, regulate moving and stationary emissions sources based, among other things, on the opacity of their emissions. Consequently, these agencies generally require periodic testing of diesel engines to ensure they continue to meet exhaust emissions requirements. Further, the opacity of exhaust plumes can be useful as an indicator of proper engine function. Thus, exhaust opacity measurements are important to diesel engine manufacturers, service technicians and diesel engine owners to help ensure that an engine is being properly maintained and tuned.

In general, opacity measurement methods for exhaust plumes can be divided into two broad categories; 1) full flow measurement and 2) partial flow measurement. The typical full flow measurement system consists of a beam of light from a light source that traverses an exhaust plume to a detector. The source and detector are generally affixed to a rigid frame or fixture which is, in turn, either mounted on the emission source or fixedly attached to some arrangement which allows the source to be positioned such that the diesel exhaust plume can pass undisturbed between the light source and the detector. There are numerous problems associated with this method of exhaust plume opacity measurement, having generally to do with accurate determination of the center of the plume with respect to the light source and detector.

In the partial flow measurement system for determining opacity of an exhaust plume, a portion of the exhaust plume is diverted by a probe and hose assembly into a sampling tube where the opacity measurement is made. While this method of exhaust opacity measurement does overcome some of the disadvantages of the full flow system in that alignment problems are eliminated, it also suffers from several drawbacks. Namely, the system is costly, it requires frequent maintenance, is subject to corrosion from sample condensation within the sampling tube and is awkward to use.

While each of these aforementioned exhaust plume opacity measurement systems has its individual advantages and disadvantages, they both suffer from the same general disadvantage namely, they require installation within the aggressive environment of the emission source itself and require the emissions source to be stationary in order to make an opacity measurement. For example, the current state-of-the-art method for measuring the opacity of exhaust emissions from diesel locomotives is the Wager opacity meter. In operation, the meter is attached to the locomotive smoke stack. In order to use this method for measuring diesel engine exhaust emissions, the locomotive must be moved onto a siding so that the instrument may be attached to the stack. For large nonstationary emission sources such as diesel locomotives this is undesirable. Not only is this process time consuming (generally requiring anywhere from 2–4 hours) but also it requires that the locomotive be withdrawn from service which is expensive and further, the opacity meter is subjected to the corrosive and erosive atmosphere in and near the smoke stack.

There have been numerous attempts to overcome the problems associated with measurement of the opacity of exhaust plumes set forth above. By way of example, U.S. Pat. No. 5,363,198 discloses a method for overcoming problems associated with full flow measurements of the opacity of exhaust plumes by employing two beams of light projected in two mutually perpendicular directions, thereby enabling the determination of the position of maximum opacity as well as the diameter of the plume at the point of maximum opacity. However, the apparatus must be mounted on the stack itself and the source must be stationary.

U.S. Pat. No. 4,647,780 discloses apparatus, wherein exhaust opacity is measured by drawing a sample of exhaust through a duct having a light source and detector located on opposite sides of the duct such that the light source directs a beam of light across the duct through the exhaust sample to the photodetector. The photodetector produces a signal whose strength is proportional to the intensity of the light beam transmitted through the exhaust sample. However, as set forth above, the apparatus requires frequent maintenance due to contamination of optical components and corrosion from sample condensation.

U.S. Pat. No. 4,432,649 recognizes the problems associated with contamination of optical surfaces associated with transmission measurements of the opacity of exhaust plumes such that false or incorrect measurements of opacity can be obtained. Disclosed therein is an apparatus for transmission measurements of stationary sources, wherein the signal transmission and receiving devices are accommodated within respective housings sealingly closed by windows which can be moved cyclically into and out of the light beam. In this way it is proposed that contamination of optical surfaces can be accounted for. However, there is no way to take into account refraction of the light beam by the hot exhaust gases, whereby the entire light beam can be shifted such that it is no longer centered on the detector and consequently, the entire light beam is no longer being measured.

What is needed is a method for monitoring exhaust emissions from large nonstationary sources, such as diesel locomotives, without moving them from the mainline track and without having to stop or slow the locomotive or train. Further, the monitoring method should be free from extraneous influences such as changes in optical properties of component parts and the need for extensive calibration procedures.

In order to make accurate measurements of an exhaust plume opacity of a moving emissions source several criteria must be considered. By way of example, the velocity of a locomotive moving down a mainline track and the dimensions of its exhaust stack fix the minimum time available for a measurement of the opacity of the exhaust plume at about 10 milliseconds. In order to be useful not only as an indicator of engine performance but also as a monitoring tool for regulatory agencies, it is necessary that the opacity of the exhaust plume be measured with an accuracy of ≈2% even in bright sunlight. The light source must be sufficiently intense to carry out an opacity measurement of this accuracy within the time scale set forth above, but not pose a safety hazard to personnel. Further, the light source must be sufficiently well collimated such that it can span the double tracks of a main railroad line (a distance of approximately 40 feet) and still be collected by a detector of reasonable size. The instrument must be sensitive enough such that an accurate measurement of total opacity of the exhaust plume can be made even if all the smoke is coming from one or two bad cylinders. The light beam from the light source must not be refracted by the hot exhaust gases to such a degree that it moves off the detector lens. It is desirable that the opacity meter only function during passage of an emissions source rather than continuously. Therefore, activation of the light source must be synchronized with the passage of a single or multiple locomotive(s) past the measurement point. The instrument must also be capable of measuring exhaust emissions from all the locomotives on multilocomotive train and must be able to correlate a given opacity measurement with a given locomotive. Finally, the instrument must be capable of withstanding the rigors of field operation.

Responsive to these needs, the present invention discloses an opacity meter that is capable of accurate measurement of the exhaust plume opacity of moving emissions sources, that is free from extraneous influences such as changes in optical properties of component parts and the need for extensive calibration procedures, that operates only during passage of an emissions source rather than continuously, that is capable of measuring exhaust emissions from all the locomotives on multilocomotive train and that can correlate a given opacity measurement with a given locomotive.

SUMMARY OF THE INVENTION

The present invention is directed toward a novel method and apparatus for measuring the opacity of exhaust plumes from diesel locomotives or other large nonstationary emission sources while they are in motion and correlating an opacity measurement with a given emissions source.

In operation, a light source is activated at a time prior to the arrival of an emissions source (e.g., a diesel locomotive) at a measurement point such that the opacity measurement is synchronized with the passage of the exhaust plume of the locomotive past the measurement point. A beam of light from the light source passes through the exhaust plume of the locomotive and is detected by a suitable detector, preferably a photodiode, placed directly opposite and across the span of the railroad track from the light source. In order to effect an accurate measurement of the opacity of the locomotive exhaust plume, the light source and detector are placed at an appropriate height above a railroad track such that the beam from the light source intersects the exhaust plume from the locomotive at the point just above where the plume exits the engine. The light beam is well-collimated and is preferably monochromatic, permitting the use of a narrow bandpass filter to discriminate against background light. It will be appreciated that because the beam of light from the light source must travel a distance of at least 40 feet (the separation required to span a double railroad track on the mainline) before striking the detector, the light source must provide a locally intense beam of light and further, the beam of light must be of sufficient intensity to permit accurate measurements of opacity even at high sampling rates. It will be further appreciated that the beam of light needs to be locally intense in order to provide a beam which significantly stronger than background such as would be provided by a continuous emission laser. The preferred light source is a diode laser.

As the exhaust plume passes the measurement point, intersection of the plume with the light beam will cause a decrease in intensity of the beam. The decrease in the intensity of the light beam can be correlated to the opacity of the exhaust plume by methods well known to those skilled in the art. The opacity measurement and the identification number of the locomotive, or other non-stationary diesel emission source, can then either be transmitted to a central data collection station or stored by the measurement system for later interrogation. By using an intense, continuous emission laser coupled with a high sampling rate detector (e.g., 10–100 kHz), a substantially continuous record (typically 100–1000 samples) of the plume opacity can be made during the time the locomotive is passing the measurement point ($\approx$10 ms). If the opacity of the exhaust plume changes from one side of the plume to the center, such as would be the case for exhaust plumes that are non-regular in cross section, a minimum in the measurement of the intensity of the beam of light during passage of the exhaust plume will indicate the opacity at the center of the exhaust plume.

DETAILED DESCRIPTION OF THE INVENTION

The present invention discloses an opacity meter useful for measuring the opacity of the exhaust plume of non-stationary emissions source such as a locomotive or any other diesel engine while in motion.

A light source is activated at a time prior to the arrival of one or more diesel locomotive(s) at a measurement point, by means of a track trigger switch or an automatic equipment identification system, such that the opacity measurement is synchronized with the passage of the locomotive(s) past the measurement point. Those familiar with the railroad industry will recognize that the automatic equipment identification system, or AEI, was developed to track the location, type, destination, schedule, and cargo of railroad rolling stock. AEI systems are typically located at railroad terminals and railroad yards and are used to permit the yardmaster to rapidly identify cars and locomotives in order to effectively manage these resources. The system is based on radio frequency transponder "tags" placed on the sides of cars and locomotives and a microprocessor-based tag reader. The transponder tags carry unique machine readable codes individually identifying each car, and respond to interrogation commands from proximally mounted tag readers. A beam of light from a light source passes through the exhaust plume of the locomotive and is detected by a suitable light detector, preferably a photodiode having a high sampling rate (10–100 kHz) capability. A receiving lens, positioned in front of the light detector, is provided to cause the beam of light to strike the center of the detector even if the beam of light is refracted by hot exhaust gases. The beam of light is well-collimated and is preferably monochromatic, permitting the use of a narrow bandpass filter to discriminate against background light (i.e., sunlight). In order to span a double railroad track and provide a beam of light that is substantially more intense than background a continuous emission laser, preferably a diode laser, can be used to provide a locally intense beam of light of sufficient intensity to permit accurate measurements of opacity, even at high sampling rates. Also included is a computer control system useful for data acquisition, calculation of opacity, manipulation and storage of opacity data, and transmission of these opacity data and the identification of the locomotive associated with that opacity data to a central data collection center. In order to perform the function disclosed herein it is necessary that operation of the opacity meter be synchronized with the arrival of a locomotive, regardless not only where in the train the locomotive is located but also the number of locomotives included in the train.

Figure 1:
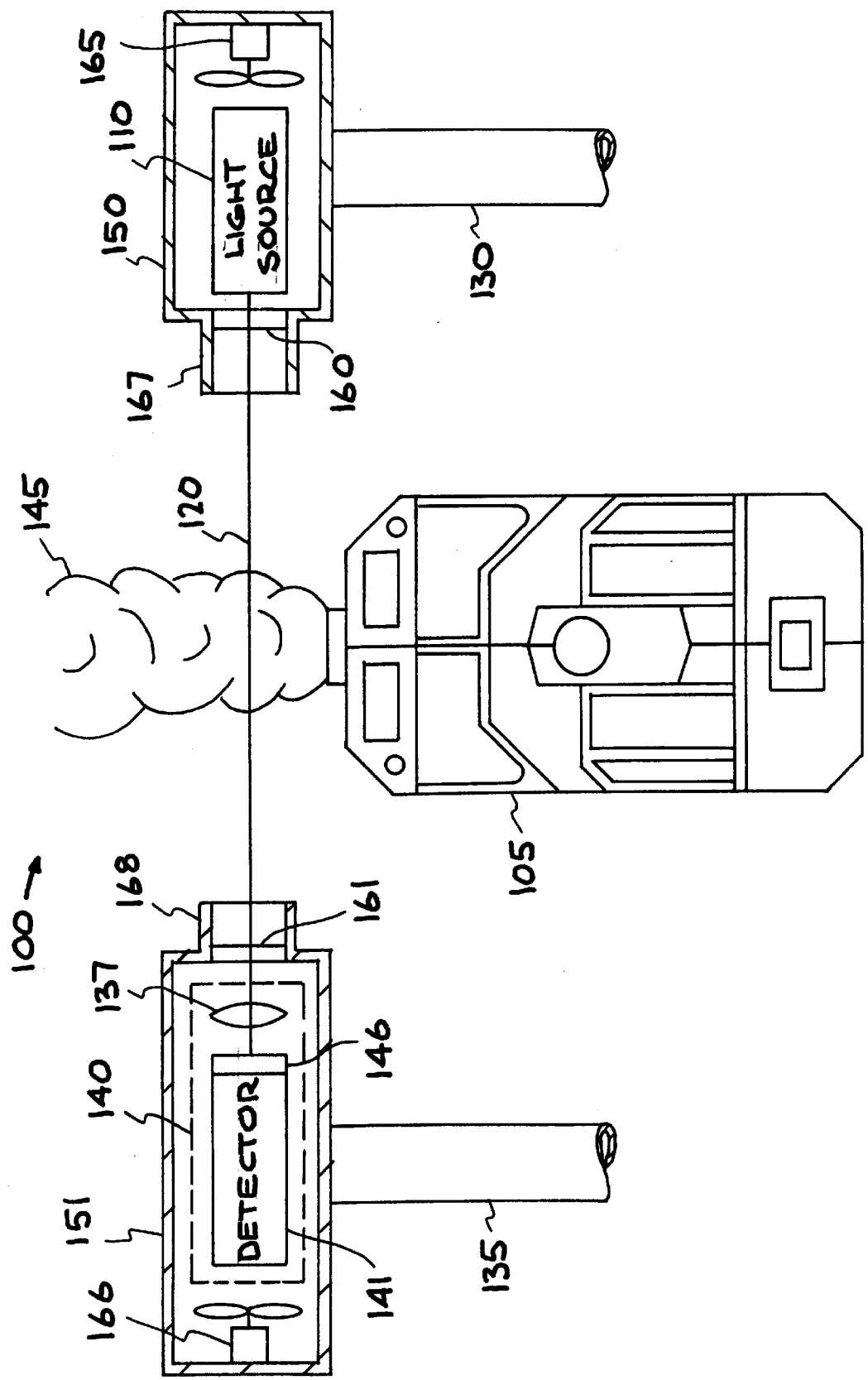
FIG. 1 shows the operation of the instant invention.

Referring now to FIG. 1, which depicts generally the operation of the present invention and the relationship between various components of the opacity meter. When locomotive 105 approaches opacity meter 100, passage past a sensing device such as a track trigger switch or (AEI) system (not shown) causes an activating signal to be sent to a control computer (not shown). The control computer then activates shutters 160 and 161 in housing 150 and 151 causing them to open and activates light source 110 to emit a beam of light 120, thereby permitting acquisition of background light and ambient opacity readings and initiating sampling by the opacity meter. Light source 110 can be a laser having an intensity such that in bright sunlight beam of light 120 can be distinguished from background light after having passed through exhaust plume 145. It is desirable to have a high intensity light source such that readings having an accuracy of 1–2% at the sampling rate required by this application (10–100 μs/sample) can be achieved. Either a diode laser or a green HeNe laser can be useful as a light source. A diode laser is preferred as a light source for this application because of its rugged nature. Directly opposite to and across railroad tracks from light source 110 and mounted on tower 135 is light receiver assembly 140 which receives beam of light 120.

At the present time, every locomotive is equipped with an (AEI) system which sends out a signal containing the unique identification code for each locomotive encoded within the AEI signal. A preferred embodiment is to use the AEI signal to initiate the opacity measurement as set forth above (i.e., notifying the control computer that a locomotive is arriving so that shutters 160 and 161 can be opened and light source 110 activated). This embodiment further provides for associating each locomotive's unique identification code with its individual opacity reading for the record.

Detector assembly 140 comprises receiving lens 137 that keeps beam of light 120 focused onto detector 141, preferably a photodiode having a high rate capability (10–100 μs/sample), to detect beam of light 120 and measure its intensity prior to arrival of the locomotive and after beam of light 120 has passed through exhaust plume 145. Associated with and directly in front of detector 141 is a narrow bandpass filter 146 which acts to filter out the solar spectrum except at the substantially one wavelength emitted by light source 110. In a preferred embodiment, both light source 110 and detector 141 are housed in weather-proof housing 150 and 151 respectively, wherein the interior of housing 150 and 151 and components contained therein can be maintained clean and dust-free by mechanical shutters 160 and 161 which remain closed until an activating signal from the computer control system is received. Upon receiving the activating signal, shutters 160 and 161 are opened and fans 165 and 166 can be activated to maintain the interior of housing 150 and 151 and associated components substantially dust-free. To provide further protection against wind and dust and to shade against direct sunlight from entering, tubes such as 167 and 168 can be mounted at the opening to housing 150 and 151. Also included with detector 141 is a computer control system (not shown) useful for control of the opacity meter system, data acquisition, manipulation, storage and transmission.

Figure 2:
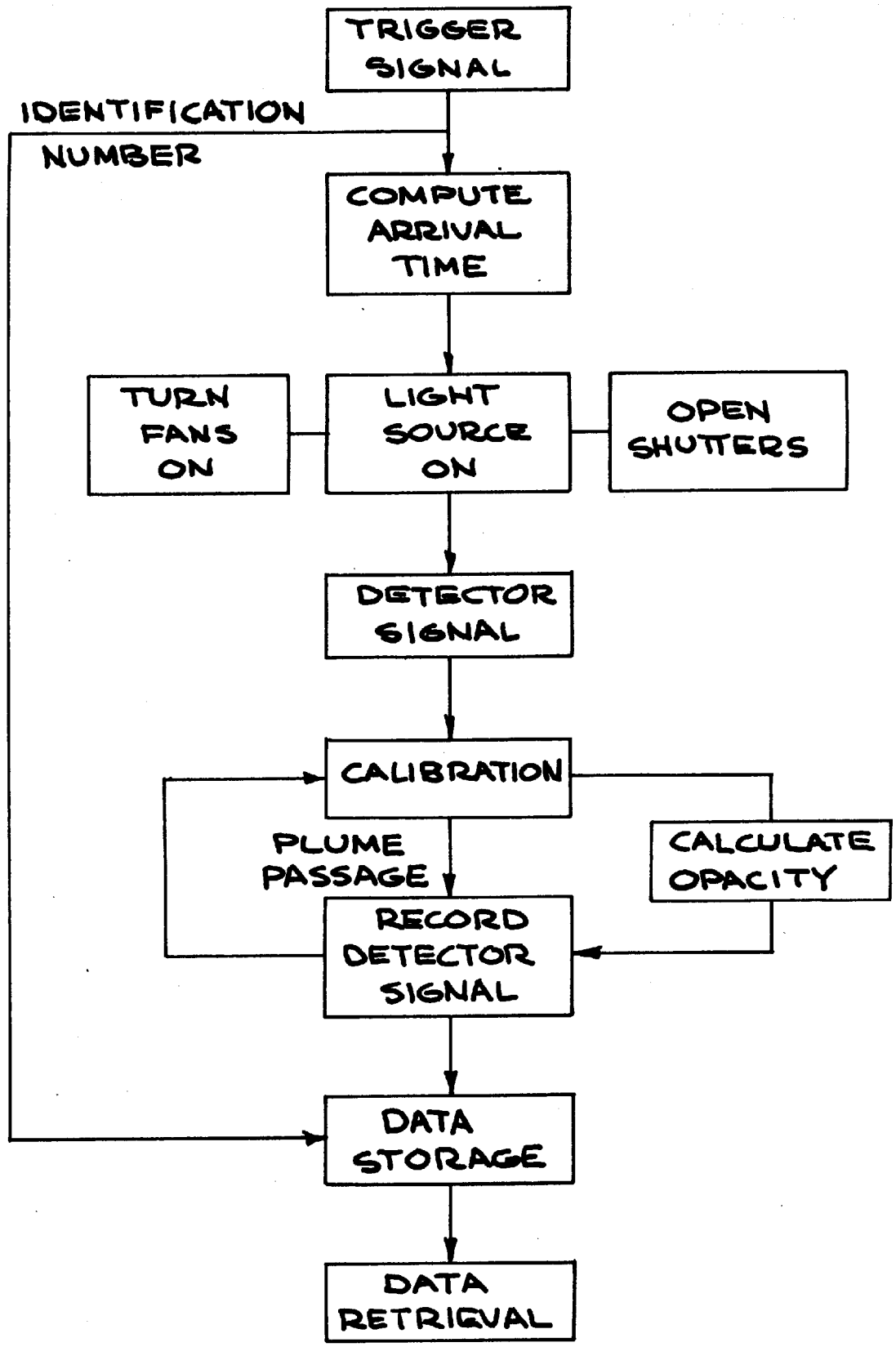
FIG. 2 illustrates flow of information through the system.

A computer control system provides the central control for opacity meter 100. As shown in FIG. 2, this includes, but is not limited to:

1) receiving track trigger(s) and computing the train speed to estimate arrival time at opacity meter 100;
2) sending out a signal to open shutters 160 and 161, turn on fans 165 and 166 and power up light source 110, thereby causing a beam of light to be emitted;
3) initiating opacity meter self-calibration procedure to determine background light level and laser intensity at 100% transmission;
4) measuring and recording detector signal during the approximately 10 ms interval exhaust plume 145 passes through beam of light 120;
5) storing the data record along with the locomotive identification, obtained either from the AEI number or the time and locomotive position;
6) repeating the initial calibration measurements to ensure that neither light source 110, nor the response of detector 141, or background light have changed during the measurement period;
7) applying corrections to the data;
8) searching the data record to determine the opacity at the center of exhaust plume 145;
9) calculating the opacity at the center of the plume from the equation $$\text{Opacity} = 1 - (Dp - B)/(Do - B)$$

where:
Dp=the detector reading in the center of the plume
Do=the detector reading with no plume
B=background reading 10) storing the locomotive identification (either the AEI number) and opacity reading for later collection or for automatic down-loading via modem to a central database.

A series of preliminary tests were carried out using a prototype of the opacity meter described and disclosed herein to determine the effect of having a majority of smoke coming from one bad cylinder and the degree to which the beam of light from the source was refracted by the hot exhaust gas of a locomotive traveling down the track.

Because the opacity measurement time (≈10 msec) on a moving locomotive will only be a small fraction of a complete engine cycle, the reading will not be accurate if all the smoke is coming from one bad cylinder and the exhaust gases are not well mixed. The test results showed that by the time the exhaust exits the stack it was sufficiently mixed that even for the case where all the smoke was coming from one cylinder and the measurement coincided with the minimum or maximum point of the cyclic fluctuation, the error would be no more than 3.5% in total opacity for an average opacity of 20%.

As the locomotive travels down the track air resistance will cause the exhaust plume to be directed toward the rear of the train. In order to minimize the effect of the motion of the locomotive on the position of the exhaust plume, vis-à-vis the measuring point, it is necessary to make the opacity measurements as close to the stack exit point as possible. However, by doing so the possibility of refraction of the beam of light by the hot exhaust gases is raised. Therefore, a test was done to determine the degree to which the beam of light was refracted by the hot exhaust gas of a locomotive traveling down the track. These tests showed that the exhaust gases did not deflect the beam of light more than about 1 inch from its original location on the detector. This small deflection of the light beam was compensated for by receiving lens 137.

From the foregoing description, one skilled in the art can readily ascertain the essential characteristics of the present invention. The description is intended to be illustrative of the present invention and are not to be construed as a limitation or restriction thereon, the invention being delineated in the following claims.

I claim:

1. An opacity meter for measuring opacity of an exhaust plume emanating from a moving source of emissions, comprising:
   a) a light source transmitting a collimated beam of light located at a first measurement point, said point having a height, said light source further located on one side of a travel path of said moving source of emissions, said moving source emitting an exhaust plume, said light source for transmitting a collimated beam of light, said collimated light beam having an intensity, said collimated light beam further having an axis lying substantially across said travel path;
   b) a light receiver means adapted to detect and measure said collimated light beam intensity, said light receiver means located at a second measurement point lying on a side opposite said one side of said travel path, said second point having a height substantially the same as said first point height, said light receiver means having an axis, said collimated light beam and said light receiver means in coaxial alignment defining an open light path, said height of said first and second measurement points chosen to locate said light path above said moving source such that said exhaust plume will pass through said collimated light beam; and
   c) means for activating said light source such that said collimated light beam is received by said light receiver means prior to arrival of said moving source between said first and second measurement points.

2. The opacity meter of claim 1, wherein said light source has sufficient intensity such that said light receiver means can be sampled at a rate of about between 1 and 100 kHz with an accuracy of greater than about 2%.

3. The opacity meter of claim 2, wherein said light source is a continuous emission laser.

4. The opacity meter of claim 3, wherein said laser is a diode laser.

5. The opacity meter of claim 3, wherein said laser is a green HeNe laser.

6. The opacity meter of claim 1, wherein said activating means comprises a track trigger switch.

7. The opacity meter of claim 1, wherein the activating means comprises an automatic equipment identification system.

8. The opacity meter of claim 3, wherein said light receiver means further includes, a light detecting means for generating a response signal in proportion to said collimated light beam intensity, a narrow bandpass filter means for eliminating background light having wavelengths other than those of said collimated light beam, and a lens means for centering said collimated light beam onto said light detecting means.

9. The opacity meter of claim 8, further including:
   means for calibrating said opacity meter by obtaining a measure of collimated light beam intensity when said collimated light beam is not blocked by said exhaust plume.

10. The opacity meter of claim 9, further including means for obtaining a measure of the opacity of the exhaust plume comprising:
    a) means for acquiring a trigger signal and computing an arrival time of said moving source of emissions;
    b) means for controlling said activating means;
    c) means for initiating said calibrating means;
    d) means for recording and manipulating said detecting means response signal;
    e) means for receiving and storing an identification code identifying said moving source;
    f) means for determining the minimum signal response during transit of said exhaust plume;
    g) computation means for calculating opacity of said exhaust plume;
    h) means for storing data, said data comprising said moving source identification code and said moving source exhaust plume opacity; and
    i) means for communicating with and transferring said data to a computer means at a separate location.

11. The opacity meter of claim 1, further including first and second housing means, each said housing means having an interior, said first housing means for accommodating said light source, said second housing means for accommodating said light receiver means, wherein each said housing means contains a shutter means for opening said housing means interior to said light path and for sealingly closing said housing means interior.

12. The opacity meter of claim 11, further including first and second fan means for maintaining said interior of said first and second housing means and said light source and said light receiver means, contained therein, substantially dust free.

13. A method for determining the opacity of an exhaust plume emitted from a moving source of emissions, comprising the steps of:
    a) opening a shutter means prior to the arrival of said moving source of emissions, detecting a background light intensity by a light detecting means, said detecting means generating a response signal in proportion to said detected light intensity, designating said signal response generated by said background light intensity as a first signal response;
    b) activating a light source, said light source emitting a collimated light beam, centering said collimated light beam onto said light detecting means by a lens means, detecting an unobscured intensity of said collimated light beam by said light detecting means, designating said light detecting means signal response generated by said unobscured intensity as a second signal response;
    c) detecting the change in said collimated light beam intensity, by said light detecting means, as said collimated light beam is partially blocked by said exhaust plume, designating said light detecting means signal response generated by the greatest detected intensity change as a third signal response; and
    d) determining an opacity of said exhaust plume by calculating a quantity equal to said second response signal less said thrid response signal divided by a quantity equal to said second response signal less said first response signal.

14. The method of claim 13 wherein said light source is a continuous emission laser.

15. The method of claim 14, wherein said laser is a diode laser.

16. The method of claim 13 wherein the step of opening further comprises receiving a signal from an activating means.

17. The method of claim 16 wherein said activating means is a track trigger switch.

18. The method of claim 16 wherein said activating means is an automatic equipment identification system.

19. The method of claim 13, further including performing the steps of:

a) determining an arrival time of said moving source;

b) activating said light source;

c) calibrating said light detecting means;

d) recording said response signals from light detecting means;

e) receiving and recording an identification code identifying said moving source; and f) storing said moving source identification code and said calculated opacity for subsequent retrieval.

* * * * *